US012734185B2

(12) United States Patent
Priebe et al.

(10) Patent No.: US 12,734,185 B2
(45) Date of Patent: Sep. 15, 2026

(54) METHOD OF TREATING VIRAL INFECTIONS WITH HEXOSE TYPE MONOSACCHARIDES AND ANALOGS THEREOF

(71) Applicants: Board of Regents, The University of Texas System, Austin, TX (US); Moleculin Biotech, Inc., Houston, TX (US)

(72) Inventors: Waldemar Priebe, Houston, TX (US); Izabela Fokt, Houston, TX (US); Rafal Zielinski, Houston, TX (US); Stanislaw Skora, Houston, TX (US); Donald Picker, Houston, TX (US); Walter Klemp, Houston, TX (US)

(73) Assignees: BOARD OF REGENTS, THE UNIVERSITY OF TEXAS SYSTEM, Austin, TX (US); MOLECULIN BIOTECH, INC., Houston, TX (US)

( * ) Notice: Subject to any disclaimer, the term of this patent is extended or adjusted under 35 U.S.C. 154(b) by 812 days.

(21) Appl. No.: 17/906,459

(22) PCT Filed: Mar. 16, 2021

(86) PCT No.: PCT/US2021/022622

§ 371 (c)(1),
(2) Date: Sep. 15, 2022

(87) PCT Pub. No.: WO2021/188586

PCT Pub. Date: Sep. 23, 2021

(65) Prior Publication Data

US 2023/0130134 A1 Apr. 27, 2023

Related U.S. Application Data

(60) Provisional application No. 62/990,337, filed on Mar. 16, 2020.

(51) Int. Cl.

| | |
|---|---|
| ***A61K 31/7004*** | (2006.01) |
| ***A61K 31/70*** | (2006.01) |
| ***A61K 31/7008*** | (2006.01) |
| ***A61K 31/7012*** | (2006.01) |
| ***A61P 31/14*** | (2006.01) |
| ***A61P 31/18*** | (2006.01) |

(52) U.S. Cl.
CPC .......... *A61K 31/7004* (2013.01); *A61K 31/70* (2013.01); *A61K 31/7008* (2013.01); *A61K 31/7012* (2013.01); *A61P 31/14* (2018.01); *A61P 31/18* (2018.01)

(58) Field of Classification Search
CPC ............................ A61K 31/7004; A61P 31/12
See application file for complete search history.

(56) References Cited

U.S. PATENT DOCUMENTS

| | | | | |
|---|---|---|---|---|
| 4,315,001 | A | 2/1982 | Blough | |
| 4,603,122 | A | 7/1986 | Blough | |
| 4,612,303 | A | 9/1986 | Homma et al. | |
| 6,231,889 | B1 | 5/2001 | Richardson et al. | |
| 6,979,675 | B2 | 12/2005 | Tidmarsh | |
| 7,160,865 | B2 | 1/2007 | Lampidis et al. | |
| 8,071,645 | B2 | 12/2011 | Newell et al. | |
| 8,299,033 | B2 | 10/2012 | Priebe et al. | |
| 8,927,506 | B2 | 1/2015 | Priebe et al. | |
| 9,149,449 | B2 | 10/2015 | Ko | |
| 9,149,489 | B2 | 10/2015 | Priebe et al. | |
| 2010/0130434 | A1 * | 5/2010 | Priebe .................... | A61K 31/70 514/23 |
| 2010/0152121 | A1 | 6/2010 | Priebe et al. | |
| 2011/0142914 | A1 | 6/2011 | Persaud et al. | |
| 2012/0058959 | A1 | 3/2012 | Brown et al. | |
| 2018/0243246 | A1 | 8/2018 | Martin | |
| 2020/0027757 | A1 | 1/2020 | Lin | |
| 2020/0276216 | A1 | 9/2020 | Goldberg | |
| 2020/0397805 | A1 | 12/2020 | Stockl et al. | |
| 2021/0008105 | A1 | 1/2021 | Martin | |
| 2021/0228750 | A1 | 7/2021 | Popovtzer | |
| 2021/0260086 | A1 | 8/2021 | Senter et al. | |
| 2021/0386666 | A1 | 12/2021 | Nyambura et al. | |
| 2022/0031719 | A1 | 2/2022 | Sheaff et al. | |
| 2022/0183971 | A1 | 6/2022 | Haruta et al. | |
| 2022/0211734 | A1 | 7/2022 | Sackstein et al. | |
| 2022/0362272 | A1 | 11/2022 | Stockl et al. | |
| 2023/0330118 | A1 | 10/2023 | Rieske et al. | |
| 2024/0316082 | A1 | 9/2024 | Stockl et al. | |

FOREIGN PATENT DOCUMENTS

| | | | |
|---|---|---|---|
| CA | 2932237 | C | 12/2022 |
| CN | 102149388 | A | 8/2011 |
| CN | 102388053 | A | 3/2012 |

(Continued)

OTHER PUBLICATIONS

Kohio, H. et al., Virology, "Glycolytic control of vacuolar-type ATPase activity: A mechanism to regulate influenza viral infection", 2013, vol. 444, pp. 301-309 (Year: 2013).*
Office Action issued in European Patent Application No. 21717687.4, dated Jul. 24, 2025.
Taylor, N. P., "Moleculin advances plan to strip and starve COVID-19," Jun. 17, 2021, retrieved from https://www.fiercebiotech.com/biotech/moleculin-advances-plan-to-strip-and-starve-covid-19.
Niemann, H. et al., "Coronavirus Glycoprotein E1, a New Type of Viral Glycoprotein," *J. Mol. Biol.*, 153 (1981): 993-1010.
Office Action issued in Chinese Patent Application No. 2021800320987, dated Oct. 30, 2024. (with English translation).
Gualdoni, G. A. et al., "Rhinovirus induces an anabolic reprogramming in host cell metabolism essential for viral replication," *PNAS*, 115.30 (2018): E7158-E7165.

(Continued)

*Primary Examiner* — Bahar Craigo
(74) *Attorney, Agent, or Firm* — pH IP Law

(57) ABSTRACT

The present invention relates to methods of treating and preventing viral diseases and infections comprising the administration of hexoses and analogs and their prodrugs thereof that inhibit glycolysis and/or glycosylation.

17 Claims, 2 Drawing Sheets

(56) References Cited

FOREIGN PATENT DOCUMENTS

| | | | | |
|---|---|---|---|---|
| CN | 102552540 A | | 7/2012 | |
| CN | 112220927 A | | 1/2021 | |
| CN | 114681473 A | | 7/2022 | |
| CN | 115381843 B | | 1/2023 | |
| CN | 111655267 B | | 6/2023 | |
| CN | 116459265 A | | 7/2023 | |
| CN | 116903761 A | | 10/2023 | |
| EP | 0129093 A1 | | 12/1984 | |
| EP | 0526253 B1 | | 11/2002 | |
| EP | 2445506 B1 | | 12/2014 | |
| EP | 2782585 B1 | | 12/2018 | |
| EP | 3517117 A1 | | 7/2019 | |
| EP | 3634428 B1 | | 1/2022 | |
| EP | 3970696 A1 | | 3/2022 | |
| IN | 202141038496 A | | 3/2023 | |
| JP | 2014-505058 A | | 2/2014 | |
| JP | 7359519 B2 | | 10/2023 | |
| WO | WO 1998/036741 A2 | | 8/1998 | |
| WO | WO-2004007747 A2 | * | 1/2004 | ............... C12Q 1/18 |
| WO | WO 2008/007367 A1 | | 1/2008 | |
| WO | WO 2008/131024 A1 | | 10/2008 | |
| WO | WO 2009/073843 A1 | | 6/2009 | |
| WO | WO 2009/108926 A1 | | 9/2009 | |
| WO | WO 2010/005799 A2 | | 1/2010 | |
| WO | WO 2012/097052 A2 | | 7/2012 | |
| WO | WO 2019/149436 A1 | | 8/2019 | |
| WO | WO 2020/128033 A1 | | 6/2020 | |
| WO | WO 2020/185675 A1 | | 9/2020 | |
| WO | WO 2021/034298 A1 | | 2/2021 | |
| WO | WO 2021/071932 A1 | | 4/2021 | |
| WO | WO 2021/160670 A1 | | 8/2021 | |
| WO | WO 2021/205412 A1 | | 10/2021 | |
| WO | WO 2021/211808 A1 | | 10/2021 | |
| WO | WO 2021/247703 A1 | | 12/2021 | |
| WO | WO 2022/002867 A1 | | 1/2022 | |
| WO | WO 2022/221766 A1 | | 10/2022 | |
| WO | WO 2023/037254 A1 | | 3/2023 | |
| WO | WO 2023/037254 A4 | | 3/2023 | |
| WO | WO 2023/062516 A1 | | 4/2023 | |

OTHER PUBLICATIONS

Office Action issued in Japanese Patent Application No. 2022-555959, dated Feb. 13, 2025.

Van Schalkwyk, D. A. et al., "The Inhibitory Effect of 2-Halo Derivatives of D-Glucose on Glycolysis and on the Proliferation of the Human Malaria Parasite *Plasmodium falciparum," The Journal of Pharmacology and Experimental Therapeutics*, 327.2 (2008): 511-517.

Anonymous: "COVID-19—Moleculin Biotech," May 11, 2020, retrieved from: https://web.Archive.org/web/20200511015214/https://webmoleculin.com/covid-19/ (retrievd on Jun. 21, 2021), published 2020.

Bojkova, D., "SARS-Cov-2 infected host cell proteomics reveal potential therapy targets," *Research Square*, 10.21203/rs.3.rs-17218/v1 (2020).

English Translation of Office Action issued in counterpart Eurasian Patent Application No. 202292632, dated Aug. 10, 2023.

Kang, H. T. et al., "2-Deoxyglucose: An anticancer and antiviral therapeutic, but not any more a low glucose mimetic," *Life Sciences*, 78 (2006): 1392-1399.

PCT International Search Report and Written Opinion issued in International Patent Application No. PCT/US2021/022622, mailed Jul. 8, 2021.

PCT International Preliminary Report on Patentability issued in International Patent Application No. PCT/US2021/022622, mailed Jun. 1, 2022.

Taylor, N. P., "Moleculin advances plan to strip and starve COVID-19," Mar. 20, 2020, retrieved from https://www.fiercebiotech.com/biotech/moleculin-advances-plan-to -strip-and-starve-covid-19.

Verma, Am et al., "A combinatorial approach of a polypharmacological adjuvant 2-deoxy-D-glucose with low dose radiation therapy to quell the cytokine storm in COVID-19 management," *International Journal of Radiation Biology*, 96.11 (2020): 1323-1328.

Ahadova, A. et al., "Dose-dependent Effect of 2-Deoxy-D-Glucose on Glycoprotein Mannosylation in Cancer Cells," *International Union of Biochemistry and Molecular Biology*, 67.3 (2015): 218-226.

Andresen, L. et al., "2-Deoxy d-Glucose Prevents Cell Surface Expression of NKG2D Ligands through Inhibition of *N*-Linked Glycosylation," *The Journal of Immunology*, 188 (2012): 1847-1855.

Bagdonaite, I. et al., "Global aspects of viral glycosylation," *Glycobiology*, 28.7 (2018): 443-467.

Blaas, D. et al., "Mechanism of human rhinovirus infections," *Molecular and Cellular Pediatrics*, 3.21 (2016): 1-4.

Datema, R. et al., "Interference with Glycosylation of Glycoproteins: Inhibition of Formation of Lipid-Linked Oligosaccharides In Vivo," *Biochem. J.*, 184 (1979): 113-123.

Fontaine, K. A. et al., "Dengue Virus Induces and Requires Glycolysis for Optimal Replication," *Journal of Virology*, 89.4 (2015): 2358-2366.

Schroeder, T. et al., "PET Imaging of Regional $^{18}$F-FDG Uptake and Lung Function After Cigarette Smoke Inhalation," *The Journal of Nuclear Medicine*, 48.3 (2007): 413-419.

Thaker, S. K. et al., "Viral hijacking of cellular metabolism," *BMC Biology*, 17.59 (2019): 1-15.

Watanabe, Y. et al., "Exploitation of glycosylation in enveloped virus pathobiology," *BBA—general Subjects*, 1863 (2019): 1480-1497.

Watanabe, T. et al., "Influenza virus-host interactomes as a basis for antiviral drug development," *Current Opinion in Virology*, 14 (2015): 71-78.

Watanabe, Y. et al., "Vulnerabilities in coronavirus glycan shields despite extensive glycosylation," *Nature Communications*, 11 (2020): 2688, 1-10.

Fokt, I. et al., "$_D$-Glucose and D-mannose-based metabolic probes. Part 3: Synthesis of specifically deuterated $_D$-glucose, $_D$-mannose, and 2-deoxy-$_D$-glucose," *Carbohydr Res.*, 368 (2013): 111-119.

"India authorises DRDO's oxygen dependence-lowering drug for Covid-19," (2021), accessed on Mar. 23, 2026 at https://www.pharmaceutical-technology.com/news/dcgi-approval-drdo-drug/?cf-view.

Ivens, T. et al., "Development of a homogeneous screening assay for automated detection of antiviral agents active against severe acute respiratory syndrome-associated coronavirus," *Journal of Virological Methods*, 129 (2005): 56-63.

Lampidis, T. J. et al., "Efficacy of 2-halogen substituted D-glucose analogs in blocking glycolysis and killing "hypoxic tumor cells"," *Cancer Chemother Pharmacol*, 58 (2006): 725-734.

Maschek, G. et al., "2-Deoxy-D-glucose Increases the Efficacy of Adriamycin and Paclitaxel in Human Osteosarcoma and Non-Small Cell Lung Cancers In Vivo," *Cancer Research*, 64 (2004): 31-34.

Sandulache, V. C. et al., "Glucose, not Glutamine is the Dominant Energy Source Required for Proliferation and Survival of Head and Neck Squamous Carcinoma Cells," *Cancer*, 117.13 (2011): 2926-2938.

Codo, Ana Campos, et al. "Elevated glucose levels favor SARS-CoV-2 infection and monocyte response through a HIF-1α/glycolysis-dependent axis."*Cell metabolism* 32.3 (2020):437-46.

Office Communication issued in corresponding Japanese Patent Application No.: 2022-555959, received on Aug. 3, 2026. English Translation.

* cited by examiner

METHOD OF TREATING VIRAL INFECTIONS WITH HEXOSE TYPE MONOSACCHARIDES AND ANALOGS THEREOF

REFERENCE TO RELATED APPLICATIONS

This application is a national phase application under 35 U.S.C. § 371 of International Application No. PCT/US2021/022622, filed Mar. 16, 2021, which claims the benefit of priority to U.S. Provisional Application No. 62/990,337, filed on Mar. 16, 2020, the entire content of each of which is hereby incorporated by reference.

BACKGROUND

Field of the Invention

Disclosed herein are new methods and pharmaceutical compositions for the treatment and prevention of viral infections. It has been found that hexose monosaccharides and analogs thereof can act as glucose and mannose mimics thereby inhibiting glycolysis, altering or inhibiting glycosylation, and reducing viral replication and infection.

Background of the Invention

Hexose monosaccharides such as D-mannose and D-glucose play an important biological role. Among others, monosaccharides are used to produce energy for cells so that they can replicate and are also used in the production of glycans which are key structural components of cells and viruses.

Glucose plays a key role in how virus infected cells produce energy which is needed for replication. Cells can produce energy in the presence or absence of oxygen. Cells often rely on a relatively efficient process of glycolysis to generate ATP (adenosine 5'-triphosphate) efficiently.

A recent study showed that the Rhinovirus (RV; responsible for the common cold) causes host cells to run in the anabolic state, making the rapid replication of the virus significantly dependent upon glycolysis, which is in turn highly dependent upon an ample supply of glucose. Likewise, a previous study of Dengue Virus (DENV) infected human foreskin fibroblasts cells showed that glucose consumption was increased during viral infection and that depriving infected cells of exogenous glucose reduced viral replication. Inhibition of the glycolytic pathway also reduced viral RNA synthesis. These studies suggest that inhibition of glycolysis is an important mechanism for anti-viral activity and it is thought that other viruses also force infected cells to rely on glycolysis.

Glycosylation is the process by which sugars such as mannose form complex oligosaccharides, and bind to proteins to form glycoproteins which are important components of cell membranes. Viruses use host-cell machinery to glycosylate their own proteins including viral envelope proteins. The exposed sugars, referred to as glycans, essentially envelope cells to create a "sugar-coating" and play a vital role in viral life-cycle including immune evasion by glycan shielding and enhancement of immune cell infection.

A large variety of human pathogenic viruses have extensively glycosylated envelope proteins. Such viruses include HIV-1, influenza virus, Lassa virus, corona virus, SARS, Zika virus, dengue virus, and Ebola virus. By inhibiting glycolysation and the formation of the glycan shield, one could make virus infected cells more vulnerable to attack by the immune system.

2-Deoxy-D-arabino-hexopyranose, known also as 2-deoxy-D-glucopyranose, 2-deoxy-D-mannose, and 2-deoxy-D glucose (hereinafter called "2-DG") is a so-called glucose decoy that looks like glucose but fails to perform the ultimate function of glucose. As a glucose decoy, 2-DG has been shown to inhibit glycolysis and energy production. 2-DG has also been shown to severely curtail rotovirus ("RV") and Dengue virus ("DENV") because it prevents glucose from being successfully converted into energy, so the host cell dies, and along with it, the chances for RV to replicate. Although 2-DG has been shown to possess antiviral activity in vitro, is not suitable as an effective therapy in vivo because it lacks drug-like properties that include poor pharmacokinetics, rapid metabolism, and unsatisfactory tissue and organ distribution.

Currently, the global COVID-19 pandemic shows that there is an ongoing unmet need to develop new methods of treating viral infections.

SUMMARY OF THE INVENTION

In some aspects, the present disclosure provides methods of treating and preventing viral infections comprising the administration of a therapeutically effective amount of a compound of Formula I, including esters of pyranose monosaccharides such as WP1122, which have surprisingly superior properties including increased levels of 2-DG in plasma, and superior distribution to critical organs such as the lung and brain which is important due to the fact that many human pathogenic viruses destroy lung function and can localize in the brain resulting in debilitating and often lethal consequences. The surprisingly superior plasma levels and tissue distribution can effectively increase the observed anti-viral properties of 2-DG in vivo. The present invention provides in some embodiments novel methods of treating and preventing viral infection by administering hexose-type monosaccharides and analogs thereof to patients in need thereof. Without being limited to a particular mechanism of action, it is believed that these compounds act as mimics of D-mannose and D-glucose producing a two-pronged attack to reduce viral replication: inhibiting energy production of infected cells and altering glycosylation patterns and inhibiting desired N-glycan formation.

In another aspect of the invention, there is provided a method of treating and preventing viral infections comprising the administration of a therapeutically effective amount of a compound of Formula I:

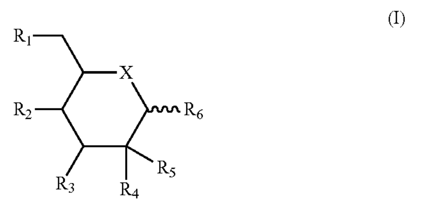

(I)

or a pharmaceutically acceptable salt thereof, wherein:

X is selected from the group consisting of O and S;

$R_1$, $R_2$, $R_3$, and $R_6$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, and carbamate, any of which may be optionally substituted;

$R_4$ and $R_5$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, carbamate, alkyl, haloalkyl, perhaloalkyl, —$N(R_7)OR_8$, —$ON(R_9)_2$, —$N(R_{10})N(R_{11})_2$, any of which may be optionally substituted, or $R_4$ and $R_5$, taken together, are selected from the group consisting of =N—$OR_{12}$ and =N—N$(R_{13})_2$; and $R_7$, $R_8$, $R_9$, $R_{10}$, $R_{11}$, $R_{12}$, and $R_{13}$ are each independently selected from the group consisting of hydrogen and alkyl, wherein said alkyl may be optionally substituted.

In a further aspect of the invention, there are provided pharmaceutical compositions for use in treating viral infections comprising administration of a therapeutically effective amount of a compound of Formula I:

(I)

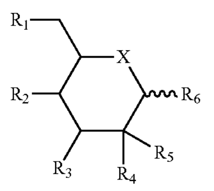

or a pharmaceutically acceptable salt thereof, wherein:

X is selected from the group consisting of O and S;

$R_1$, $R_2$, $R_3$, and $R_6$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, and carbamate, any of which may be optionally substituted;

$R_4$ and $R_5$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, carbamate, alkyl, haloalkyl, perhaloalkyl, —$N(R_7)OR_8$, —$ON(R_9)_2$, —$N(R_{10})N(R_{11})_2$, any of which may be optionally substituted, or $R_4$ and $R_5$, taken together, are selected from the group consisting of =N—$OR_{12}$ and =N—N$(R_{13})_2$; and $R_7$, $R_8$, $R_9$, $R_{10}$, $R_{11}$, $R_{12}$, and $R_{13}$ are each independently selected from the group consisting of hydrogen and alkyl, wherein said alkyl may be optionally substituted.

In a further aspect, there is provided a pharmaceutical composition for use in the manufacture of a medicament for the treatment and prevention of a viral infection in a patient comprising a compound of Formula I:

(I)

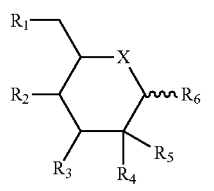

or a pharmaceutically acceptable salt thereof, wherein:

X is selected from the group consisting of O and S;

$R_1$, $R_2$, $R_3$, and $R_6$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, and carbamate, any of which may be optionally substituted;

$R_4$ and $R_5$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, carbamate, alkyl, haloalkyl, perhaloalkyl, —$N(R_7)OR_8$, —$ON(R_9)_2$, —$N(R_{10})N(R_{11})_2$, any of which may be optionally substituted, or $R_4$ and $R_5$, taken together, are selected from the group consisting of =N—$OR_{12}$ and =N—N$(R_{13})_2$; and $R_7$, $R_8$, $R_9$, $R_{10}$, $R_{11}$, $R_{12}$, and $R_{13}$ are each independently selected from the group consisting of hydrogen and alkyl, wherein said alkyl may be optionally substituted.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF THE INVENTION

Figure 1:
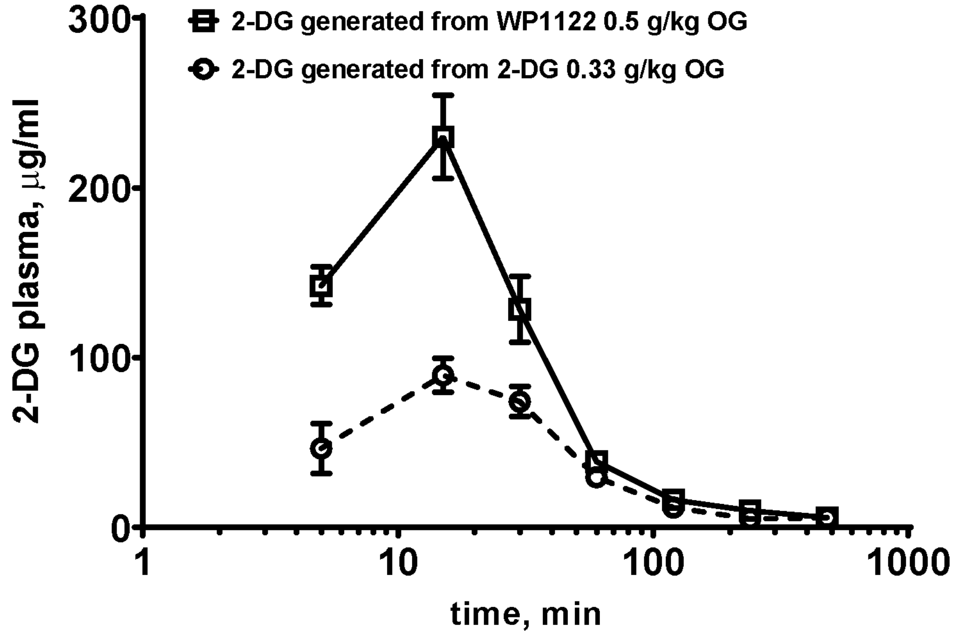
FIG. 1 shows PK (pharmacokinetic) analysis of 2-DG in plasma after oral administration of WP1122 and 2-DG.

The prevention invention provides for methods of treating and preventing viral infections in a patient in need thereof comprising administering a therapeutically effective amount of compounds have structural Formula I:

(I)

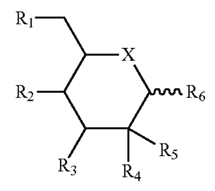

or a pharmaceutically acceptable salt thereof, wherein:

X is selected from the group consisting of O and S;

$R_1$, $R_2$, $R_3$, and $R_6$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, and carbamate, any of which may be optionally substituted;

$R_4$ and $R_5$ are independently selected from the group consisting of hydrogen, hydroxyl, thiol, halogen, alkoxy, haloalkoxy, per haloalkoxy, alkoxyalkyloxy, —OC(O)alkyl, $OCO_2$alkyl, alkylthio, amino, alkylamino, N-sulfonamido, N-amido, carbamate, alkyl, haloalkyl, perhaloalkyl, —$N(R_7)OR_8$, —$ON(R_9)_2$, —$N(R_{10})N(R_{11})_2$, any of which may be optionally substituted, or $R_4$ and $R_5$, taken together, are selected from the group consisting of ═N—$OR_{12}$ and ═N—N$(R_{13})_2$; and $R_7$, $R_8$, $R_9$, $R_{10}$, $R_{11}$, $R_{12}$, and $R_{13}$ are each independently selected from the group consisting of hydrogen and alkyl, wherein said alkyl may be optionally substituted.

In certain embodiments, the compounds have structural Formula II:

(II)

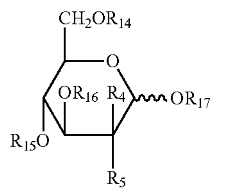

or a pharmaceutically acceptable salt thereof, wherein:

$R_{14}$, $R_{15}$, $R_{16}$, and $R_{17}$ are independently selected from the group consisting of hydrogen, $COCH_3$, $COCH_2CH_3$, and $COCH_2CH_2CH_3$; and $R_4$ and $R_5$ are independently selected from the group consisting of hydrogen, Cl, Br, I, $^{18}F$, and $^{19}F$.

In further embodiments, $R_4$ and $R_5$ are independently selected from the group consisting of hydrogen, $^{18}F$, and $^{19}F$.

In further embodiments, $R_{14}$, $R_{15}$, $R_{16}$, and $R_{17}$ are independently selected from the group consisting of hydrogen and $COCH_3$.

In certain embodiments, the compounds have structural Formula III or structural Formula IV:

(III)

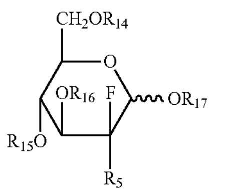

(IV)

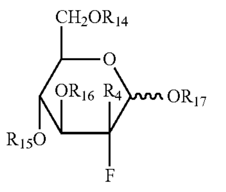

or a pharmaceutically acceptable salt thereof, wherein:

$R_{14}$, $R_{15}$, $R_{16}$, and $R_{17}$ are independently selected from the group consisting of hydrogen, $COCH_3$, $COCH_2CH_3$, and $COCH_2CH_2CH_3$;

$R_4$ and $R_5$ are independently selected from the group consisting of alkyl, lower alkyl, substituted alkyl, cycloalkyl, hydroxyl, alkoxy, acyl, alkenyl, alkylene, alkylamino, alkylthio, alkylidene, alkynyl, amido, carbamoyl, acylamino, carbamate, O-carbamyl, N-carbamyl, carbonyl, carboxy, carboxylate, ester, ether, halogen, haloalkoxy, haloalkyl, heteroalkyl, hydrazinyl, hydroxyalkyl, isocyanato, isothiocyanato, mercaptyl, nitro, oxy, $NH_2$, $NR_{18}R_{19}$, and $NHCOR_{20}$;

$R_{18}$ and $R_{19}$ are selected from the group consisting of hydrogen, alkyl, lower alkyl, substituted alkyl, cycloalkyl, acyl, alkenyl, alkylene, alkylamino, alkylthio, alkylidene, alkynyl, amido, haloalkyl, heteroalkyl, hydrazinyl, and hydroxyalkyl; and $R_{20}$ is selected from the group consisting of hydrogen, lower alkyl, substituted lower alkyl, alkenyl, alkylene, alkylamino, alkylthio, alkylidene, alkynyl, amido, carbamoyl, haloalkyl, and heteroalkyl.

In further embodiments, $R_{14}$, $R_{15}$, $R_{16}$, and $R_{17}$ are hydrogen.

In certain embodiments, the compounds have structural Formula V:

(V)

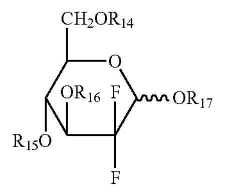

or a pharmaceutically acceptable salt thereof, wherein:

$R_{14}$, $R_{15}$, $R_{16}$, and $R_{17}$ are independently selected from the group consisting of hydrogen, $COCH_3$, $COCH_2CH_3$, and $COCH_2CH_2CH_3$.

In certain embodiments, a compound is selected from the group consisting of Examples 1 to 84.

In certain embodiments, a compound has the following structural formula:

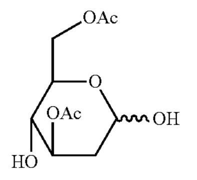

and pharmaceutically acceptable salts thereof.

In certain embodiments, the viral infection is selected from the group consisting of is caused by a virus selected from the group consisting of HIV-1, influenza virus, Lassa virus, corona virus including SARS-CoV-1, SARs-CoV-2, Zika virus, dengue virus, and Ebola virus. In certain embodiments, the viral infection is a viral infection of the respiratory tract. In certain embodiments, said patient has viral pneumonia. In certain embodiments, the viral infection is caused by SARs-CoV-2.

In certain embodiments, the patient has COVID-19.

Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)$CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl. Preferably, the "acyl" is a lower acyl meaning the carbonyl is attached to a lower alkyl group.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. In further embodiments, said alkyl will comprise 1 to 3 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms. Preferably, the term "lower" when describing an alkyl moiety refers to 1-3 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to NRR', wherein R and R are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a $RS(=O)_2NR'$— group with R and R' as defined herein.

The term "S-sulfonamido" refers to a —$S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR$— group with X is a halogen and R as defined herein.

The term "trihalomethanesulfonyl" refers to a $X_3CS(O)_2$— group where X is a halogen.

The term "trihalomethoxy" refers to a $X_3CO$— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"Glycolysis inhibitor" is used herein to refer to a compound that exhibits glycolytic activity and inhibits energy production.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a virus, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans.

Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid and the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient")

with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation or proliferation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives or a fatty acid such as steric or oleic acid together with an alcohol such as propylene glycol or a macrogel. The formulation may incorporate any suitable surface-active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface-active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for COVID-19 involving administration of one of the compounds described herein, increased therapeutic benefit may result by also providing the patient with another therapeutic agent for viral or bacterial infections, or anti-inflammatory, for example. In any case, regardless of the disease, disorder or condition being treated, the overall benefit experienced by the patient may simply be additive of the two therapeutic agents or the patient may experience a synergistic benefit.

In certain embodiments, topical steroids include, but are not limited to, clobetasol propionate, betamethasone, betamethasone dipropionate, halobetasol propionate, fluocinonide, diflorasone diacetate, mometasone furoate, halcinonide, desoximetasone, fluticasone propionate, flurandrenolide, triamcinolone acetonide, fluocinolone acetonide, hydrocortisone, hydrocortisone valerate, prednicarbate, desonide, and alclometasone dipropionate.

In certain embodiments, non-steroidal anti-inflammatory agents include, but are not limited to, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, lumiracoxib, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin.

In certain embodiments, antibacterial agents include, but are not limited to, amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristan, demeclocycline, dicloxacillin, dirithromycin, doxycycline, erythromycin, enafloxacin, ertepenem, ethambutol, flucloxacillin, fosfomycin, furazolidone, gatifloxacin, geldanamycin, gentamicin, herbimicin, imipenem, isoniazide, kanamicin, levofloxacin, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, ofloxacin, oxytetracycline, penicillin, piperacillin, platensimycin, polymixin B, prontocil, pyrazinamide, quinupristine, rifampin, retapamulin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating viral infections in a human or animal subject in need of such treatment comprising administering to said subject an amount of a compound disclosed herein effective to reduce or prevent said infection in the subject, in combination with at least one additional agent for the treatment of said disease that is known in the art. In a related aspect, certain embodiments provide therapeutic compositions comprising at least one compound disclosed herein in combination with one or more additional agents for the treatment of viral infections and conditions caused by such infection, for example pneumonia.

Specific viral diseases to be treated by the compounds, compositions, and methods disclosed herein include, but are not limited to infections of HIV, influenza virus, Lassa virus, corona virus including SARS virus, Zika virus, dengue virus, and Ebola virus. In some embodiments, the viral diseases are viral respiratory infections including viral pneumonia. In some embodiments, the viral infection is COVID 19 caused by SARs-CoV-2.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

General Synthetic Methods for Preparing Compounds

The compounds disclosed herein can be synthesized according to the procedures described in U.S. Pat. No. 8,927,506 B2 (columns 14-26); WO 2010005799 (paragraphs [0086]-[0145]); WO 2009108926 (paragraphs [0173]-[0185]); WO 2008131024 (paragraphs [0067]-[0072]); US 20100152121 (paragraphs [0067]-[0083]); U.S. Pat. No. 7,160,865 (columns 11-13); and U.S. Pat. No. 6,979,675 (columns 28-29), the disclosures of which are hereby incorporated by reference as if written herein in their entireties.

The invention is further illustrated by the following examples.

Example 1

(4R,5S,6R)-4,5-dihydroxy-6-(hydroxymethyl)tetrahydro-2H-pyran-2-yl acetate

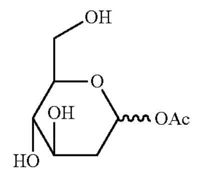

Example 2

(4R,5S,6R)-5-hydroxy-6-(hydroxymethyl)tetrahydro-2H-pyran-2,4-diyl diacetate

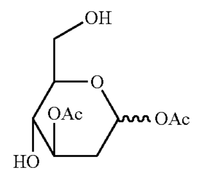

Example 3

((2R,3S,4R)-6-acetoxy-3,4-dihydroxytetrahydro-2H-pyran-2-yl)methyl acetate

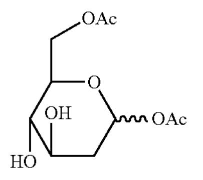

Example 4

((2R,3S,4R)-3-acetoxy-4,6-dihydroxytetrahydro-2H-pyran-2-yl)methyl acetate

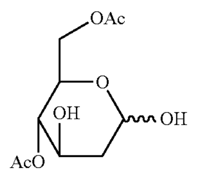

Example 5

((2R,3S,4R)-4-acetoxy-3,6-dihydroxytetrahydro-2H-pyran-2-yl)methyl acetate (WP1122)

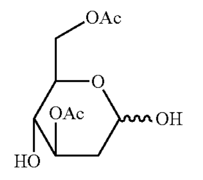

Example 6

((2R,3S,4R)-3,4,6-trihydroxytetrahydro-2H-pyran-2-yl)methyl acetate

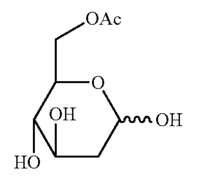

Example 7

(2R,3S,4R)-4,6-dihydroxy-2-(hydroxymethyl)tetrahydro-2H-pyran-3-yl acetate

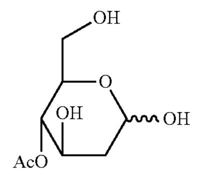

Example 8

(4R,5S,6R)-4-hydroxy-6-(hydroxymethyl)tetrahydro-2H-pyran-2,5-diyl diacetate

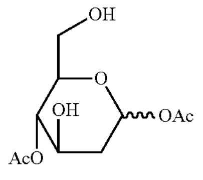

Example 9

(2R,3S,4R)-6-hydroxy-2-(hydroxymethyl)tetrahydro-2H-pyran-3,4-diyl diacetate

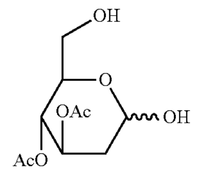

Example 10

(4R,5S,6R)-6-(acetoxymethyl)-5-hydroxytetrahydro-2H-pyran-2,4-diyl diacetate

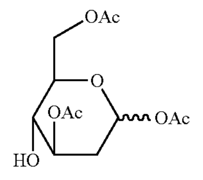

Example 11

(4R,5S,6R)-6-(hydroxymethyl)tetrahydro-2H-pyran-2,4,5-triyl triacetate

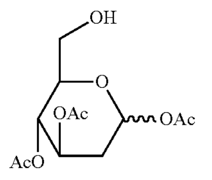

Example 12

(4R,5S,6R)-6-(acetoxymethyl)tetrahydro-2H-pyran-2,4,5-triyl triacetate

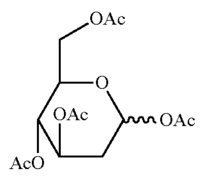

Example 13

(4S,5S,6R)-3,3-difluoro-6-(hydroxymethyl)tetrahydro-2H-pyran-2,4,5-triol (2-Deoxy-2,2-difluoro-D-arabino-hexopyranose (DFG))

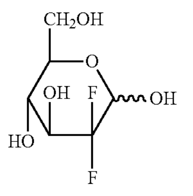

Example 14

(3R,4S,5S,6R)-6-(hydroxymethyl)-3-iodotetrahydro-2H-pyran-2,4,5-triol (2-Deoxy-2-iodo-D-glucose)

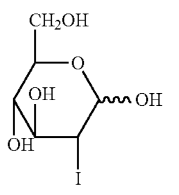

Example 15

(3S,4S,5S,6R)-6-(hydroxymethyl)-3-iodotetrahydro-2H-pyran-2,4,5-triol (2-Deoxy-2-iodo-D-mannose)

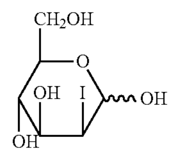

Example 16

(3R,4S,5R,6R)-6-(hydroxymethyl)-3-iodotetrahydro-2H-pyran-2,4,5-triol (2-Deoxy-2-iodo-D-galactose)

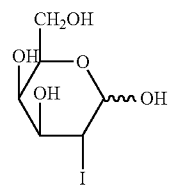

Example 17

(3S,4S,5R,6R)-6-(hydroxymethyl)-3-iodotetrahydro-2H-pyran-2,4,5-triol (2-Deoxy-2-iodo-D-talose)

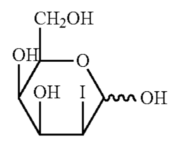

Example 18

(4R,5S,6R)-6-(hydroxymethyl)tetrahydro-2H-pyran-2,4,5-triol (2-deoxy-D-glucose)

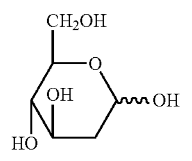

Example 19

(3S,4S,5S,6R)-3-fluoro-6-(hydroxymethyl)tetrahydro-2H-pyran-2,4,5-triol (2-Deoxy-2-fluoro-D-mannose)

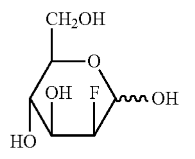

Example 20

(3R,4S,5S,6R)-3-fluoro-6-(hydroxymethyl)tetrahydro-2H-pyran-2,4,5-triol (2-Deoxy-2-fluoro-D-glucose)

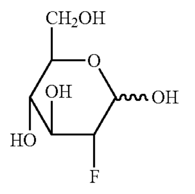

Example 21

(3R,4S,5S,6R)-3-chloro-6-(hydroxymethyl)tetrahydro-2H-pyran-2,4,5-triol (2-Deoxy-2-chloro-D-glucose)

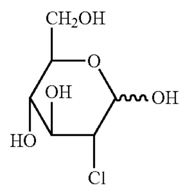

Example 22

(3S,4S,5S,6R)-3-chloro-6-(hydroxymethyl)tetrahydro-2H-pyran-2,4,5-triol (2-Deoxy-2-chloro-D-mannose)

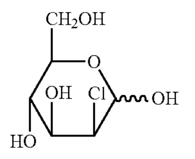

Example 23

(3R,4S,5S,6R)-3-bromo-6-(hydroxymethyl)tetrahydro-2H-pyran-2,4,5-triol (2-Deoxy-2-bromo-D-glucose)

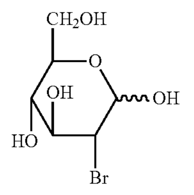

Example 24

(3S,4S,5S,6R)-3-bromo-6-(hydroxymethyl)tetrahydro-2H-pyran-2,4,5-triol (2-Deoxy-2-bromo-D-mannose)

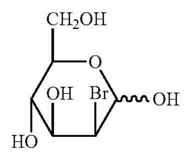

Example 25

(3R,4S,5S,6R)-6-methyltetrahydro-2H-pyran-2,3,4,5-tetraol (6-Deoxy-D-glucose)

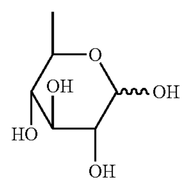

Example 26

(3R,4S,5S,6S)-6-(fluoromethyl)tetrahydro-2H-pyran-2,3,4,5-tetraol (6-Deoxy-6-fluoro-D-glucose)

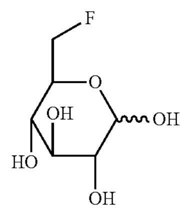

Example 27

(3R,4S,5S,6R)-6-(methoxymethyl)tetrahydro-2H-pyran-2,3,4,5-tetraol (6-O-Methyl-D-glucose)

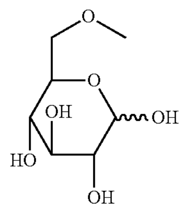

Example 28

(3R,4S,5S,6R)-2-fluoro-6-(hydroxymethyl)tetrahydro-2H-pyran-3,4,5-triol (D-Glucosyl fluoride)

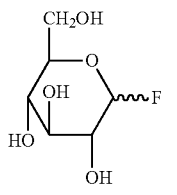

Example 29

(2R,3S,4R,5S)-2-(hydroxymethyl)tetrahydro-2H-pyran-3,4,5-triol (1-Deoxy-D-glucose)

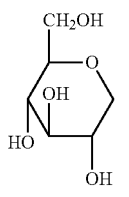

Example 30

(3R,4R,5S,6R)-5-fluoro-6-(hydroxymethyl)tetrahydro-2H-pyran-2,3,4-triol (4-Fluoro-D-glucose)

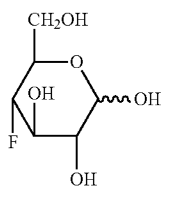

Example 31

(3R,4S,6S)-6-(hydroxymethyl)tetrahydro-2H-pyran-2,3,4-triol (4-Deoxy-D-glucose)

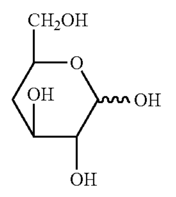

Example 32

(3S,4S,5R,6R)-4-fluoro-6-(hydroxymethyl)tetrahydro-2H-pyran-2,3,5-triol (3-Fluoro-D-glucose)

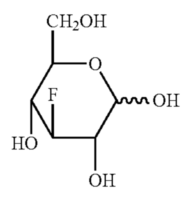

Example 33

(3R,5S,6R)-6-(hydroxymethyl)tetrahydro-2H-pyran-2,3,5-triol (3-Deoxy-D-glucose)

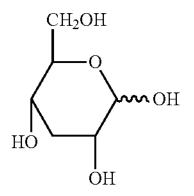 [SMILES: OCC1OC(O)C(O)CC1O]

Example 34

(3R,4S,5S,6S)-6-(mercaptomethyl)tetrahydro-2H-pyran-2,3,4,5-tetraol (6-Thio-D-glucose)

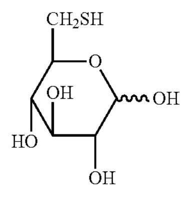

Example 35

(3R,4S,5S,6R)-6-(hydroxymethyl)tetrahydro-2H-thiopyran-2,3,4,5-tetraol (5-Thio-D-glucose)

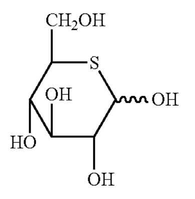

Example 36

((2R,3S,4S,5R)-3,4,5,6-tetrahydroxytetrahydro-2H-pyran-2-yl)methyl pentanoate

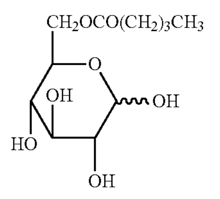

Example 37

((2R,3S,4S,5R)-3,4,5,6-tetrahydroxytetrahydro-2H-pyran-2-yl)methyl tetradecanoate

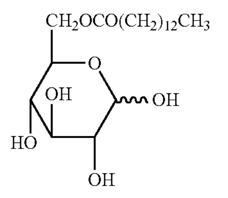

Example 38

((2R,3S,4S,5R)-3,4,5,6-tetrahydroxytetrahydro-2H-pyran-2-yl)methyl palmitate

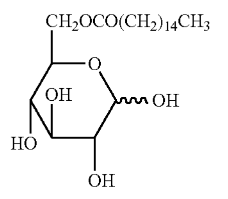

Example 39

(2R,3S,4R,5R)-4,5,6-trihydroxy-2-(hydroxymethyl) tetrahydro-2H-pyran-3-yl pentanoate

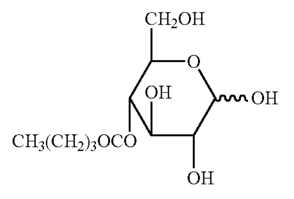

Example 40

(2S,3S,4S,5R)-tridecyl 4,5,6-trihydroxy-2-(hydroxymethyl)tetrahydro-2H-pyran-3-carboxylate

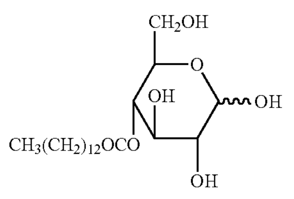

Example 41

(2R,3S,4R,5R)-4,5,6-trihydroxy-2-(hydroxymethyl) tetrahydro-2H-pyran-3-yl palmitate

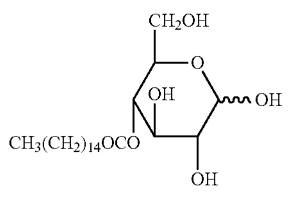

Example 42

(3R,4S,5R,6R)-2,3,5-trihydroxy-6-(hydroxymethyl) tetrahydro-2H-pyran-4-yl pentanoate

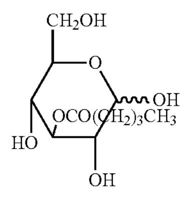

Example 43

(3R,4S,5R,6R)-2,3,5-trihydroxy-6-(hydroxymethyl) tetrahydro-2H-pyran-4-yl tetradecanoate

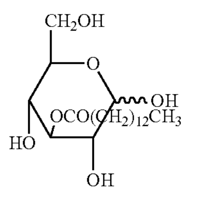

Example 44

(3R,4S,5R,6R)-2,3,5-trihydroxy-6-(hydroxymethyl) tetrahydro-2H-pyran-4-yl palmitate

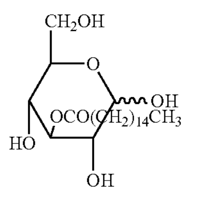

Example 45

(3R,4S,5S,6R)-3,4,5-trihydroxy-6-(hydroxymethyl) tetrahydro-2H-pyran-2-yl pentanoate

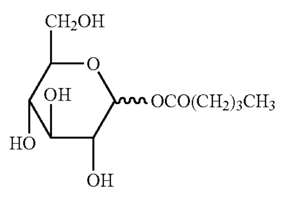

Example 46

(3R,4S,5S,6R)-3,4,5-trihydroxy-6-(hydroxymethyl) tetrahydro-2H-pyran-2-yl tetradecanoate

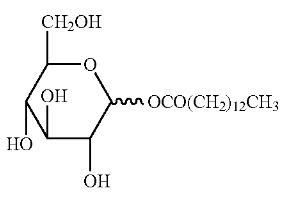

Example 47

(3R,4S,5S,6R)-3,4,5-trihydroxy-6-(hydroxymethyl) tetrahydro-2H-pyran-2-yl palmitate

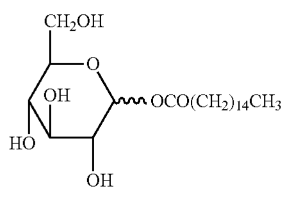

Example 48

(3R,4R,5S,6R)-3-amino-6-(hydroxymethyl)tetrahydro-2H-pyran-2,4,5-triol (2-Glucosamine)

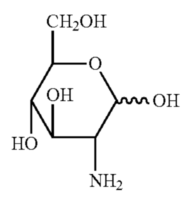

Example 49

(3R,4R,5R,6R)-3-amino-6-(hydroxymethyl)tetrahydro-2H-pyran-2,4,5-triol (2-Galactosamine)

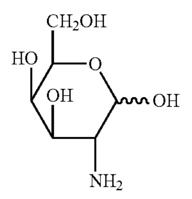

Example 50

(3S,4R,5S,6R)-3-amino-6-(hydroxymethyl)tetrahydro-2H-pyran-2,4,5-triol (2-Mannosamine)

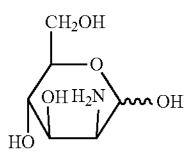

Example 51

(3S,4S,5S,6R)-3-fluoro-6-(hydroxymethyl)tetrahydro-2H-pyran-2,4,5-triol (2-Deoxy-2-fluoro-D-mannose)

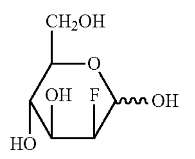

Example 52

(4R,5R,6R)-6-(hydroxymethyl)tetrahydro-2H-pyran-2,4,5-triol (2-Deoxy-D-galactose)

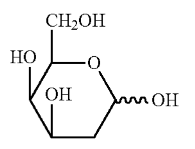

Example 53

(3R,4S,5R,6R)-3-fluoro-6-(hydroxymethyl)tetrahydro-2H-pyran-2,4,5-triol (2-Deoxy-2-fluoro-D-galactose)

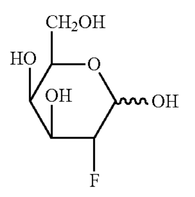

Example 54

N-((3R,4R,5S,6R)-2,4,5-trihydroxy-6-(hydroxymethyl)tetrahydro-2H-pyran-3-yl)methanesulfonamide

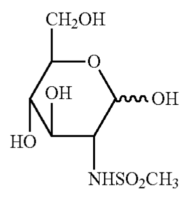

Example 55

N-((3S,4R,5S,6R)-2,4,5-trihydroxy-6-(hydroxymethyl)tetrahydro-2H-pyran-3-yl)methanesulfonamide

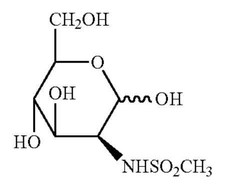

Example 56

(3R,4R,5S,6R)-6-(hydroxymethyl)-3-methyltetrahydro-2H-pyran-2,4,5-triol

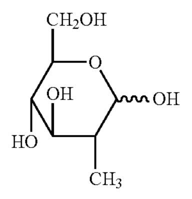

Example 57

(3R,4R,5S,6R)-3-(fluoromethyl)-6-(hydroxymethyl)tetrahydro-2H-pyran-2,4,5-triol

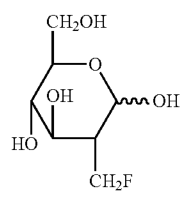

Example 58

(3R,4R,5S,6R)-3-(difluoromethyl)-6-(hydroxymethyl)tetrahydro-2H-pyran-2,4,5-triol

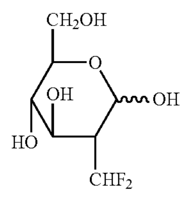

Example 59

(3R,4R,5S,6R)-6-(hydroxymethyl)-3-(trifluoromethyl)tetrahydro-2H-pyran-2,4,5-triol

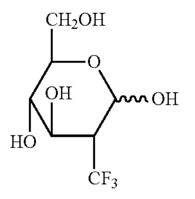

Example 60 (3S,4R,5S,6R)-6-(hydroxymethyl)-3-methyltetrahydro-2H-pyran-2,4,5-triol

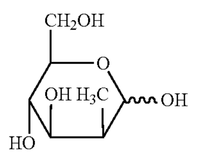

Example 61

(3S,4R,5S,6R)-3-(fluoromethyl)-6-(hydroxymethyl)tetrahydro-2H-pyran-2,4,5-triol

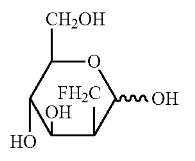

Example 62

(3S,4R,5S,6R)-3-(difluoromethyl)-6-(hydroxymethyl)tetrahydro-2H-pyran-2,4,5-triol

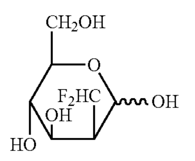

Example 63

(3S,4R,5S,6R)-6-(hydroxymethyl)-3-(trifluoromethyl)tetrahydro-2H-pyran-2,4,5-triol

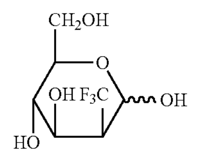

Example 64

(3S,4S,5S,6R)-6-(hydroxymethyl)-3-methyltetrahydro-2H-pyran-2,3,4,5-tetraol

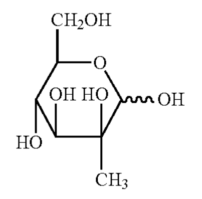

Example 65

(3S,4S,5S,6R)-3-(fluoromethyl)-6-(hydroxymethyl)tetrahydro-2H-pyran-2,3,4,5-tetraol

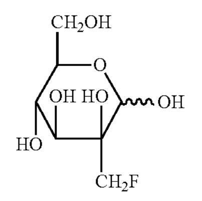

Example 66

(3S,4S,5S,6R)-3-(difluoromethyl)-6-(hydroxymethyl)tetrahydro-2H-pyran-2,3,4,5-tetraol

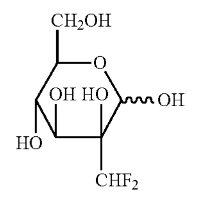

Example 67

(3S,4S,5S,6R)-6-(hydroxymethyl)-3-(trifluoromethyl)tetrahydro-2H-pyran-2,3,4,5-tetraol

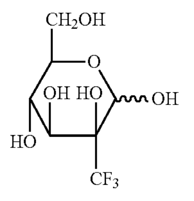

Example 68

(3R,4S,5S,6R)-6-(hydroxymethyl)-3-methyltetrahydro-2H-pyran-2,3,4,5-tetraol

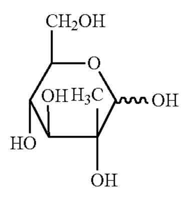

Example 69

(3R,4S,5S,6R)-3-(fluoromethyl)-6-(hydroxymethyl) tetrahydro-2H-pyran-2,3,4,5-tetraol

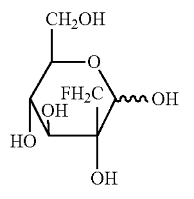

Example 70

(3R,4S,5S,6R)-3-(difluoromethyl)-6-(hydroxymethyl)tetrahydro-2H-pyran-2,3,4,5-tetraol

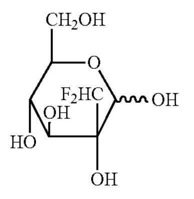

Example 71

(3R,4S,5S,6R)-6-(hydroxymethyl)-3-(trifluoromethyl)tetrahydro-2H-pyran-2,3,4,5-tetraol

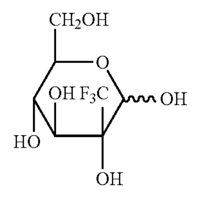

Example 72

N-((3R,4R,5S,6R)-2,4,5-trihydroxy-6-(hydroxymethyl)tetrahydro-2H-pyran-3-yl)acetamide

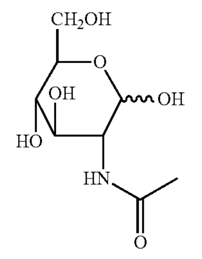

Example 73

(3R,4S,5S,6R)-3-(aminooxy)-6-(hydroxymethyl) tetrahydro-2H-pyran-2,4,5-triol

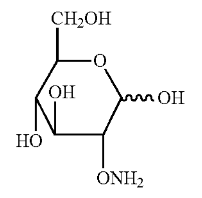

Example 74

(3S,4S,5S,6R)-3-(aminooxy)-6-(hydroxymethyl) tetrahydro-2H-pyran-2,4,5-triol

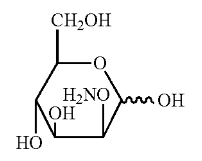

Example 75

(3R,4R,5S,6R)-3-(hydroxyamino)-6-(hydroxymethyl)tetrahydro-2H-pyran-2,4,5-triol

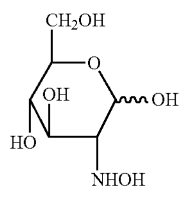

Example 76

(3S,4R,5S,6R)-3-(hydroxyamino)-6-(hydroxymethyl)tetrahydro-2H-pyran-2,4,5-triol

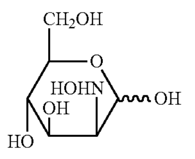

Example 77

(3R,4R,5S,6R)-3-hydrazinyl-6-(hydroxymethyl) tetrahydro-2H-pyran-2,4,5-triol

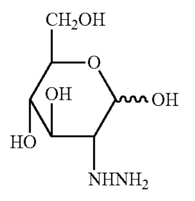

Example 78

(3S,4R,5S,6R)-3-hydrazinyl-6-(hydroxymethyl)tetrahydro-2H-pyran-2,4,5-triol

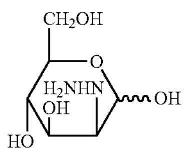

Example 79

(3R,4S,5S,6R)-6-(hydroxymethyl)-3-mercaptotetrahydro-2H-pyran-2,4,5-triol

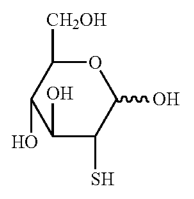

Example 80

(3S,4S,5S,6R)-6-(hydroxymethyl)-3-mercaptotetrahydro-2H-pyran-2,4,5-triol

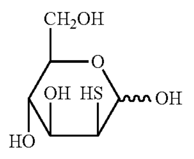

Example 81

(4R,5S,6R)-3-hydrazono-6-(hydroxymethyl)tetrahydro-2H-pyran-2,4,5-triol

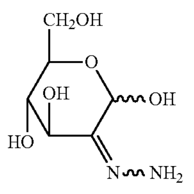

Example 82

(4R,5S,6R)-2,4,5-trihydroxy-6-(hydroxymethyl) dihydro-2H-pyran-3(4H)-one oxime

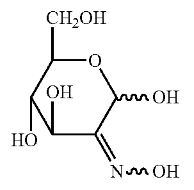

Example 83

(2R,3S,4R)-2-(acetoxymethyl)-6-hydroxytetrahydro-2H-pyran-3,4-diyl diacetate

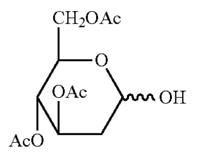

Example 84

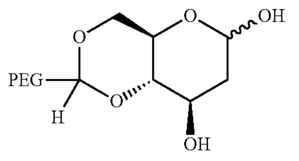

Biological Examples

Example A

Pharmacokinetic Studies of WP1122 and In Vivo Conversion to 2-DG

Analytical methodologies (LC/MS) have been developed that are capable of quantifying concentrations of the compounds of the present invention and/or the liberation of 2-DG in plasma.

Experimental procedures Absorption and pharmacokinetic studies of WP1122 and 2-DG were investigated in female CD-1 mice. The mice were dosed orally with equimolar doses of WP1122 and 2-DG, 0.5 g/kg and 0.33 g/kg, respectively. Individual groups of animals are sacrificed at indicated time points (n=5/time point) following dose administration. From each animal plasma, skin, and other tissues are harvested and the concentration of 2-DG was measured by LC/MS.

Results. The peak plasma level of 2-DG was achieved 15 min after administration of WP1122 or 2-DG, with maximum concentration of 230 and 89.5 μg/mL for WP1122 and 2-DG respectively. Half-life of the 2-DG in plasma was 252 and 137.7 for WP1122 and 2-DG. Similarly AUC values recorded for WP1122 was nearly twice higher than corresponding level measured for 2-DG. FIG. 1 shows PK analysis of 2-DG in plasma after oral administration of WP1122 and 2-DG. PK parameters for both compounds have been summarized in Table 1.

TABLE 1

PK parameters of 2-DG in plasma generated from WP1122 or 2-DG after oral administration.

| Compound | $T_{1/2}$ (min) | $T_{Max}$ (min) | $C_{Max}$ (μg/mL) | $AUC_{Last}$ (min*μg/mL) | $AUC_{Inf}$ (min*μg/mL) |
|---|---|---|---|---|---|
| 2-DG generated from WP1122 | 252 | 15 | 230 | 11956 | 14065 |

TABLE 1-continued

PK parameters of 2-DG in plasma generated from WP1122 or 2-DG after oral administration.

| Compound | $T_{1/2}$ (min) | $T_{Max}$ (min) | $C_{Max}$ (μg/mL) | $AUC_{Last}$ (min*μg/mL) | $AUC_{Inf}$ (min*μg/mL) |
|---|---|---|---|---|---|
| 2-DG generated from 2-DG | 137.7 | 15 | 89.5 | 6841.7 | 7928.7 |

Example B

Comparison of WP1122 and 2-DG Levels in Lungs after Intravenous Administration

Experimental procedures. The pharmacokinetic and tissue organ distribution of WP1122 and 2-DG labeled with tritium was analyzed in male Sprague-Dawley rats. Animals (n=3 per timepoint) were dosed intravenously with 2-DG or WP1122 at equimolar dose 0.2 and 0.13 g/kg for WP1122 and 2-DG respectively. The animals were euthanized at 15, 30, 60 min and 6- and 24-hours post-dose. The organs were extracted, rinsed with PBS and radioactivity was measured using Liquid Scintillation Counting (LCS).

Figure 2:
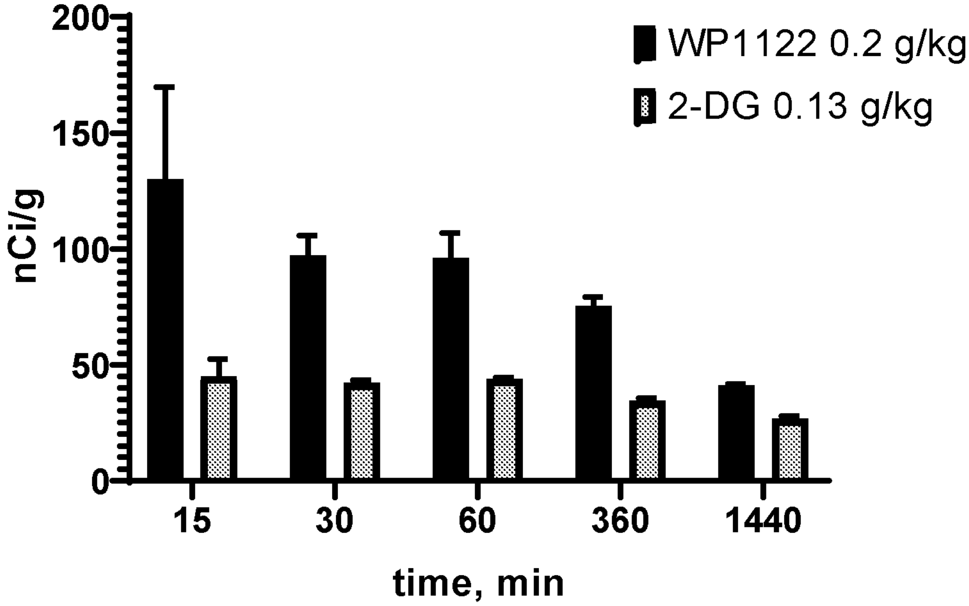
FIG. 2 shows a graphical comparison of 2-DG and metabolites from both WP1122 and 2-DG found in the lungs of rats at different time points after i.v. administration of radiolabeled drugs.

Results. The 2-DG and metabolites from both WP1122 and 2-DG have been detected in lungs in all tested timepoints. The highest concentration of radiolabeled compounds was observed for WP1122 in 15 min post injection and was nearly three times higher than radioactivity obtained from 2-DG administration. Increased presence of metabolites were observed in for WP1122 in all time points including 24 hours after administration. (See, FIG. 2).

This experiment demonstrates the surprisingly superior distribution of esters of pyranose monosaccharides such as WP1122 in the lung making it superior for use in treating viral infections targeting the lung such as COVID 19.

All references cited herein, including patents, patent applications, and publications, are hereby incorporated by reference in their entireties, whether previously specifically incorporated or not.

The various features and embodiments of the present invention, referred to in individual sections above apply, as appropriate, to other sections, mutatis mutandis. Consequently, features specified in one section may be combined with features specified in other sections, as appropriate.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A method of treating a viral infection comprising the administration, to a patient in need thereof, of a therapeutically effective amount of a compound of Formula II (II)

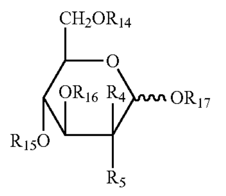

or a pharmaceutically acceptable salt thereof, wherein:

a) $R_{14}$, and $R_{16}$, are independently selected from the group consisting of $COCH_3$, $COCH_2CH_3$, and $COCH_2CH_2CH_3$;
$R_{15}$, $R_{17}$, $R_4$ and $R_5$ are hydrogen; and
wherein said viral infection is caused by SARS-COV-2; or b) $R_{14}$, and $R_{16}$, are independently selected from the group consisting of hydrogen, $COCH_3$, $COCH_2CH_3$, and $COCH_2CH_2CH_3$;
$R_{15}$, and $R_{17}$ are hydrogen; and
one of $R_4$ and $R_5$ is hydrogen and the other of $R_4$ and $R_5$ is I;
wherein said viral infection is caused by a virus selected from the group consisting of HIV-1 virus, Lassa virus, corona virus, Zika virus, Dengue virus, and Ebola virus.

2. The method of claim 1, wherein said compound of Formula II is a compound according to group b).

3. The method of claim 2, wherein $R_{14}$ and $R_{16}$ are independently selected from the group consisting of hydrogen and $COCH_3$.

4. The method of claim 1, wherein the compound Formula II is selected from the group consisting of ((2R,3S,4R)-4-acetoxy-3,6-dihydroxytetrahydro-2H-pyran-2-yl) methyl acetate, 2-Deoxy-2-iodo-D-glucose, and 2-Deoxy-2-iodo-D-mannose, and pharmaceutically acceptable salts thereof.

5. The method of claim 1, wherein said compound has the structural formula:

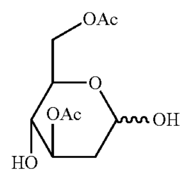

and pharmaceutically acceptable salts thereof.

6. The method of claim 2, wherein said viral infection is caused by a corona virus.

7. The method of claim 6, wherein said viral infection is caused by SARs-COV-2.

8. The method of claim 4, wherein said viral infection is caused by a virus characterized by glycosylated envelope proteins on infected cells.

9. The method of claim 4, wherein the patient has COVID-19.

10. The method of claim 4, wherein the patient tests positive for COVID-19.

11. The method of claim 4, wherein the patient is asymptomatic.

12. The method of claim 1, wherein the compound is administered by inhalation or insufflation.

13. The method of claim 4, wherein said compound of Formula II is ((2R,3S,4R)-4-acetoxy-3,6-dihydroxytetrahydro-2H-pyran-2-yl) methyl acetate, and pharmaceutically acceptable salts thereof, and said viral infection is caused by SARS-COV-2.

14. The method of claim 4, wherein said compound of Formula II is 2-Deoxy-2-iodo-D-mannose, and pharmaceutically acceptable salts thereof, and said viral infection is caused by SARs-COV-2, or Ebola.

15. The method of claim 2, wherein $R_{14}$ and $R_{16}$ are independently selected from the group consisting of hydrogen and $COCH_3$; and pharmaceutically acceptable salts therein; wherein said viral infection is caused by a corona virus.

16. The method of claim 15, wherein said viral infection is caused by SARs-COV-2.

17. The method of claim 15, wherein the compound is administered by inhalation or insufflation.

* * * * *